US008078245B2

(12) United States Patent
Daly et al.

(10) Patent No.: US 8,078,245 B2
(45) Date of Patent: Dec. 13, 2011

(54) EXTENDED FOCAL REGION MEASURING APPARATUS AND METHOD

(75) Inventors: Daniel John Daly, Wokingham (GB); Graeme Lawrence Clark, Shenfield (GB)

(73) Assignee: Lein Applied Diagnostics Limited, Berkshire (GB)

( * ) Notice: Subject to any disclaimer, the term of this patent is extended or adjusted under 35 U.S.C. 154(b) by 1499 days.

(21) Appl. No.: 10/582,648

(22) PCT Filed: Nov. 24, 2004

(86) PCT No.: PCT/GB2004/004946
§ 371 (c)(1), (2), (4) Date: Jun. 12, 2006

(87) PCT Pub. No.: WO2005/058152
PCT Pub. Date: Jun. 30, 2005

(65) Prior Publication Data
US 2007/0123761 A1 May 31, 2007

(51) Int. Cl.
*A61B 5/1455* (2006.01)
*G01B 9/00* (2006.01)
(52) U.S. Cl. .................. 600/319; 356/124; 600/310
(58) Field of Classification Search .......... 600/309–344
See application file for complete search history.

(56) References Cited

U.S. PATENT DOCUMENTS

| 3,958,560 | A | 5/1976 | March | 600/319 |
|---|---|---|---|---|
| 3,963,019 | A | 6/1976 | Quandt | 600/319 |
| 4,014,321 | A | 3/1977 | March | 600/319 |
| 4,154,114 | A | 5/1979 | Katz | 73/629 |
| 4,407,008 | A | 9/1983 | Schmidt | 348/79 |
| 4,750,830 | A | 6/1988 | Lee | 351/211 |
| 4,806,004 | A | 2/1989 | Wayland | 359/389 |
| 5,152,759 | A | * 10/1992 | Parel et al. | 606/5 |

(Continued)

FOREIGN PATENT DOCUMENTS

EP 0589191 8/1984

(Continued)

OTHER PUBLICATIONS

Anumula, H., Nezhuvingal, A., Li, Y., Cameron, B., "Development of a Non-invasive Corneal Birefringence Compensated Glucose Sensing Polarimeter", Proc. SPIE vol. 4958, p. 303-312, Advanced Biomedical and Clinical Diagnostic Systems, Jul. 2003.

(Continued)

*Primary Examiner* — Eric Winakur
*Assistant Examiner* — Marjan Fardanesh
(74) *Attorney, Agent, or Firm* — Chapin IP Law, LLC

(57) ABSTRACT

A method and apparatus for measuring an apparent depth of a section of an animal body are disclosed. Light is focused concurrently to an extended focal region comprising a plurality or continuum of measurement locations. Light reflected by a refractive index interface coincident with one of the plurality of measurement locations is detected. Detected light signals are generated from light reflected from first and second interfaces respectively defining the section under investigation, so that the apparent positions of the interfaces may be derived. A confocal arrangement and an axicon element may be employed. Preferably, the section is the aqueous humor of an eye. From changes in its refractive index corresponding changes in glucose concentration in the aqueous humor and, in turn, in the bloodstream of a patient may be derived, offering a non-invasive monitoring means for diabetic patients. Other compounds and structures of the body may alternatively be investigated.

14 Claims, 6 Drawing Sheets

U.S. PATENT DOCUMENTS

| | | | |
|---|---|---|---|
| 5,209,231 A | 5/1993 | Cote | 600/310 |
| 5,433,197 A | 7/1995 | Stark | 600/319 |
| 5,553,617 A | 9/1996 | Barkenhagen | 600/318 |
| 5,582,168 A | 12/1996 | Samuels | 600/407 |
| 5,785,651 A | 7/1998 | Kuhn | 600/310 |
| 5,820,557 A | 10/1998 | Hattori | 600/319 |
| 5,880,465 A | 3/1999 | Boettner | 250/234 |
| 5,961,449 A | 10/1999 | Toida | 600/319 |
| 6,066,847 A | 5/2000 | Rosenthal | 250/252.1 |
| 6,152,875 A | 11/2000 | Hakamata | 600/319 |
| 6,181,957 B1 | 1/2001 | Lambert | 600/319 |
| 6,187,599 B1 | 2/2001 | Asher | 436/531 |
| 6,188,477 B1 | 2/2001 | Pu | 356/491 |
| 6,267,477 B1 | 7/2001 | Karpol | 351/221 |
| 6,382,794 B1 | 5/2002 | Lai | 351/212 |
| 6,424,850 B1 | 7/2002 | Lambert | 600/319 |
| 6,442,410 B1 | 8/2002 | Steffes | 600/319 |
| 6,574,501 B2 | 6/2003 | Lambert | 600/473 |
| 6,585,723 B1 | 7/2003 | Sumiya | 606/5 |
| 6,836,337 B2 | 12/2004 | Cornsweet | 356/517 |
| 6,853,854 B1 | 2/2005 | Proniewicz | 600/319 |
| 6,934,035 B2 | 8/2005 | Yang | 356/485 |
| 6,961,599 B2 | 11/2005 | Lambert | 600/318 |
| 2002/0171804 A1 | 11/2002 | Rathjen | 351/221 |
| 2003/0211625 A1 | 11/2003 | Cohan | 436/95 |
| 2003/0225321 A1 | 12/2003 | Cote | 600/318 |
| 2003/0233036 A1 | 12/2003 | Ansari | 600/316 |
| 2004/0080759 A1 | 4/2004 | Shaver | 356/609 |
| 2004/0087843 A1 | 5/2004 | Rice | 600/319 |
| 2004/0138539 A1 | 7/2004 | Jay | 600/322 |
| 2004/0152963 A1 | 8/2004 | March | 600/319 |
| 2004/0257585 A1 | 12/2004 | Cornsweet | 356/517 |
| 2004/0260159 A1 | 12/2004 | Gerlitz | 600/319 |

FOREIGN PATENT DOCUMENTS

| | | |
|---|---|---|
| GB | 2 144 537 | 3/1985 |
| WO | WO 93/07801 | 4/1993 |
| WO | WO 97/13448 | 4/1997 |
| WO | 97/30627 | 8/1997 |
| WO | WO 99/44496 | 9/1999 |
| WO | WO 00/60350 | 10/2000 |
| WO | WO 2004/034894 A1 | 4/2004 |
| WO | WO 2004/064628 | 8/2004 |
| WO | WO 2005/120334 | 12/2005 |

OTHER PUBLICATIONS

Arnold, M., "Noninvasive Laser Measurement of Blood Glucose in the Eye: A Bright idea or an Optical Illusion", Diabetes Technology and Therapeutics, vol. 1, No. 2, 1999.

Baba, J., Cameron, B., Cote, G., "Effect of temperature, pH, and corneal birefringence on polarimetric glucose monitoring in the eye", Journal of Biomedical Optics 7(3), 321-328 (Jul. 2002).

Baba, J., Cote, G., "Dual-detector polarimetry for Compensation of Motion Artifact in a Glucose Sensing System", Optical Diagnostics and Sensing of Biological Fluids and Glucose and Cholesterol Monitoring II, Proc. SPIE vol. 4624 (2002), pp. 76-80.

Bockle, S., Rovati, L., Ansari, R., "Polarimetric glucose sensing using the Brewster-reflection off the eye lens: theoretical analysis", Proceedings of SPIE—vol. 4624 Optical Diagnostics and Sensing of Biological Fluids and Glucose and Cholesterol Monitoring II, May 2002, pp. 160-164.

Borchert M, Storrie-Lombardi M, Lambert J "A non-invasive glucose monitor: preliminary results in rabbits" Diabetes Technology & Therapeutics 1999; 1: 145-151.

Cameron, B., Gorde, M., Satheesan, B., Cote, G., "The Use of Polarized Laser Light Through the Eye for Noninvasive Glucose Monitoring", Diabetes Technology and Therapeutics, vol. 1, No. 2, 1999.

Chou C, Lin P-K "Noninvasive glucose monitoring with optical heterodyne Technique" Diabetes Technology & Therapeutics 2000; 2: 45-47.

Cote, G., "Non-Invasive and Minimally Invasive Optical Monitoring Technologies", Symposium of Innovative Non- or Minimally Invasive Technologies for Monitoring Health and Nutritional Status in Mothers and Young Children, Aug. 2000, Children's Research Center, Baylor College of Medicine, Houston, TX.

Khalil, O., "Non-Invasive Glucose Measurement Technologies: An Update from 1999 to the Dawn of the New Millennium", Diabetes Technology and Therapeutics, vol. 6, No. 5, 2004, pp. 660-697.

Li, H., Petroll, W., Moller-Pederson, T., Maurer, J, Cavanagh, H., Jester, J., "Epithelial and Corneal Thickness Measurements by in vivo confocal microscopy through focusing (CMTF)", Current Eye Research; (16): 214-221, 1997.

Li, J., Jester, J., Cavanagh, H., Black, T., Petroll, W., "On-Line 3-Dimensional Confocal Imaging in Vivo", Investigative Ophthalmology and Visual Science, Sep. 2000, vol. 41, No. 10, pp. 2945-2953.

Liu, J., Bagherzadeh, M., Hitzenberger, C., Pircher, M., Zawadzki, R., Fercher, A., "Glucose dispersion measurement using white-light LCI", Coherence Domain Optical Methods and Optical Coherence Tomography in Biomedicine VII, Proceedings of the SPIE, vol. 4956, pp. 348-351 (2003).

March, W., "Analysis: A Noninvasive Ocular Glucose Sensor", Diabetes Technology & Therapeutics, Jun. 2001, vol. 3, No. 2: 209-210.

March, W., Mueller, A., Herbrechtsmeier, P., "Clinical Trial of a Non-invasive Contact Lens Glucose Sensor", Diabetes Technology and Thrapeutics, vol. 6, No. 6, 2004, pp. 782-789.

March, W., Ochsner, K., Horna, J., "Intraocular Lens Glucose Sensor", Diabetes Technology & Therapeutics, May 2000, vol. 2, No. 1: 27-30.

Masters, B. and Bohnke, M., "Three-Dimensional Confocal Microscopy of the Living Human Eye", Annu. Rev. Biomed. Eng. 2002, 4:69-91.

McLaren, J., Nau, C., Erie, J., Bourne, W., "Corneal Thickness Measurement by Confocal Microscopy, Ultrasound, and Scanning Slit Methods", American Journal of Ophthalmology, Jun. 2004, pp. 1011-1020.

McLaren, J., Nau, C., Erie, J., Bourne, W., "Corneal Thickness Measurement by Confocal Microscopy, Ultrasound, and Scanning Slit Methods", American Journal of Ophthalmology, Feb. 2005, pp. 391-392, Editorial Response.

Rawer, R., Stork, W., Kreiner, C., "Non-invasive polarimetric measurement of glucose concentration in the anterior chamber of the eye", Graefe's Arch Clin Exp Ophthalmol (2004) 242: 1017-1023.

Schrader W, Meuer P, Popp J, Kiefer W, Menzebach J-U, Schrader B "Non-invasive glucose determination in the human eye" Journal of Molecular Structure 2005; 735-736: 299-306.

Sebag, J., Ansari, R., Dunker, S., Suh, K., "Dynamic Light Scattering of Diabetic Vitreopathy", Diabetes Technology and Therapeutics, vol. 1, No. 2, 1999.

Steffes P "Laser-based measurement of glucose in the ocular aqueous humor: an efficacious portal for determination of serum glucose levels" Diabetes Technology & Therapeutics 1999; 1: 129-133.

Wicksted JP, Erckens RJ, Motamedi M, and March WF. "Raman spectroscopy studies of metabolic concentrations in aqueous solutions and aqueous humor specimens" Applied Spectroscopy 49:987-993, 1995.

* cited by examiner

EXTENDED FOCAL REGION MEASURING APPARATUS AND METHOD

CROSS REFERENCE TO RELATED APPLICATIONS

This Patent Application claims priority to PCT Application No. PCT/GB2004/004946 filed on Nov. 24, 2004, the contents and teachings of which are hereby incorporated by reference in their entirety.

BACKGROUND AND SUMMARY

The present invention relates to an extended focal region measurement apparatus and method, for application especially, but not exclusively, to the investigation of the structure and composition of regions of the human body.

Diabetes is a major and rapidly growing problem: there are estimates that over 170 million people suffer from the disorder worldwide. In addition, studies have shown that the incidence of juvenile-onset, insulin-dependent diabetes has doubled over the last 15 years. There has also been a doubling in the number of children under the age of 5 suffering from diabetes in just 10 years.

The symptoms associated with diabetes can be severe. If the blood glucose level is not suitably controlled by the patient, the physical damage which may be caused includes blindness, heart disease and gangrene. As such, the mortality rate for diabetics is significantly higher than the rate for the average person.

A person's blood glucose concentration varies over a relatively short timescale, due to a number of factors, such as the length of time since the patient's last meal, the type of food ingested, the amount of exercise taken, and whether or not the patient is otherwise ill. As a result, diabetics usually need to test their glucose levels many times a day, in order to monitor and control their condition. The actual testing regime varies between patients and is individually prescribed by the doctor or diabetes educator of the patient.

The primary method used for testing blood glucose concentration involves the taking of a blood sample, which is then analysed. In this test, a patient's finger or arm is pricked with a small needle and the resulting drop of blood is placed on a test strip, for analysis in a hand-held meter. If the glucose concentration reading is above an acceptable level, insulin must be injected into the blood stream to bring the glucose concentration back within an acceptable range.

Because of the frequency of testing required to monitor the blood glucose concentration, the patient is normally expected to perform the tests throughout the day, drawing and analysing the blood sample himself. There are a number of problems experienced by patients with the above procedure. Firstly, the technique is invasive and therefore carries the risk of infection. Secondly, continual pricking of the fingers causes hard skin. Thirdly, the process is clearly not pain-free. Finally, there is a large, ongoing consumables cost associated with this method. As a result of these and other problems, certain sectors of the diabetic population do not test themselves as often as required. This is particularly the case for the elderly, who tend to lack the fine motor skills required; teenagers, who tend to find the whole procedure socially embarrassing; and children, who tend not to accept the discomfort associated with the process.

A number of non-invasive blood glucose concentration measuring techniques have been proposed to overcome these problems. One particular approach which has been suggested involves measuring the glucose concentration of the aqueous humor in the anterior chamber of the eye, since, while varying between individuals, there is a close correlation between this concentration and the blood glucose concentration. Measurement of the glucose concentration of the aqueous humor may be achieved by various means; for example, by polarimetry (e.g., U.S. Pat. No. 5,896,198); by Raman techniques (e.g., WO-A-00/02479); by spectrometry (e.g., U.S. Pat. No. 5,969,815); or by reflectometry (e.g., U.S. Pat. No. 6,236,089).

A desirable alternative approach to measuring the glucose concentration in the aqueous humor involves measuring the refractive index of the aqueous humor, since there is a strong correlation between the refractive index and the glucose concentration.

U.S. Pat. No. 3,963,019 discloses a method and apparatus, by which a beam of light is projected into and through the aqueous humor of a patient's eye. The angular displacement of light reflected from the iris and through the aqueous humor is proportional to the refractive index of the aqueous humor. Hence by measuring the angle of the reflected light, the glucose concentration of the aqueous humor may be found. In practice, this technique measures the combined optical properties of the aqueous humor and the cornea and it is not trivial to deconvolve the effect of each. In addition, changes to the cornea, for example, will reduce the accuracy of readings taken in this way.

U.S. Pat. No. 6,152,875 discloses a method and apparatus, by which the refractive index of the aqueous humor may be derived by measuring the intensity of light reflected from the eye. The intensities of reflected light from the air/cornea and cornea/aqueous humor interfaces are measured and compared to determined how much light is reflected from the cornea/aqueous humor interface relative to the cornea/air interface. It is assumed that the amount of light reflected from the air/cornea interface is constant and that the amount of light reflected from the cornea/aqueous humor interface is related to the refractive index of the aqueous humor. There are a number of practical limitations to this technique. For example, any stray light or reflections from other surfaces will cause inaccuracies in measurements, so additional steps such as interferometry, frequency shift, or ultra-short pulses are required to achieve the required accuracy. Since the method relies on the measurement of the relative reflected intensities from two surfaces of the eye, further inaccuracies may be introduced because of diurnal variations in the shape of the cornea, changes in the refractive index of the tear film (itself affected by the blood glucose level) and variations in atmospheric conditions, such as temperature and pressure, which will alter the refractive index of the air.

WO-A-03/025562 discloses an interferometric technique for measuring the refractive index of the aqueous humor. In this technique, two beams of light are shone onto the iris in the eye, one beam having a plane wavefront and the other beam having a spherical wavefront. The two beams interfere where they coincide on the iris, to form a pattern of dark and light rings at a detector. Changes in the refractive index of the aqueous humor affect the phase difference between the interfering beams and therefore the spacing of the fringes. The refractive index may thus be determined by measuring the spacing of the fringes. One practical problem with this technique is that a laser is required. A further problem is that interferometry is very sensitive to vibrations, with the result that the apparatus effectively needs to be arranged on an optical bench. In particular, this technique would not be suitable for use with a hand-held meter. Furthermore, with this interferometric arrangement, it is not possible to distinguish between corneal changes and changes in the aqueous humor.

There is a need, therefore, for an apparatus and method which employs a non-invasive, optical technique for the reliable determination of changes in the refractive index of the aqueous humor in the anterior chamber of an eye. In particular, it would be desirable for measurements made by such apparatus and method to be used to derive the concentration of glucose in the aqueous humor and, in turn, the concentration of glucose in the blood of a patient. There is also a need for an apparatus and method which may be used to determine the concentrations of other compounds in the aqueous humor, including both naturally occurring and intentionally introduced chemicals, and which may be used to measure other properties of the eye, such as corneal thickness. It would also be desirable for such an apparatus and method to find application additionally in the investigation of structures in other regions of the body.

The present invention aims to address the above and other objectives by providing an improved technique for the measurement of regions of a human or animal body and in particular properties of an eye.

According to a first aspect of the present invention, there is provided a method of measuring an apparent depth of a section of an animal body, the section being defined by first and second interfaces, comprising the steps: a) focusing a monochromatic incident beam of light to a plurality or continuum of measurement locations along a measurement line passing through the section, the measurement line being generated by an optical element adapted to provide an extended focal region for monochromatic light, such that incident light is focused to all measurement locations along the measurement line concurrently; b) detecting light reflected from at least one of the plurality of measurement locations when a respective interface is coincident therewith; c) generating at least a first and a second signal representative of the detected light reflected from the first and second interfaces respectively; and d) deriving from the first and second signals the apparent positions of the first and second interfaces.

When an extended focal region is generated within a region of the body, in particular the eye, incident light is reflected as a local peak when an interface between two media of different refractive indices is coincident with part of the extended focal region. By recording the signal generated by a detector on receipt of this reflected light, a reflected light intensity profile may be obtained. The signal is associated with the apparent position of the measurement location, either in time or space, so that the apparent depth of the section may be derived. The apparent depth will typically differ from the real, or physical, depth of the section by the refractive index of the section. Changes in the apparent depth may therefore be used to calculate changes in the refractive index of the section. For example, if the apparent depth is an optical path length through the aqueous humor, a change in the refractive index of the aqueous humor may be derived from a comparison of optical path length measurements, thereby providing a measure of the glucose concentration of the aqueous humor. In this case, the first and second surfaces are the cornea-aqueous humor interface and the aqueous humor-ocular lens interface respectively. Although the method and apparatus of the present invention are intended to be used predominantly with the human eye, the invention may also be applied to animal eyes or to other parts of human or animal bodies.

The present invention provides many advantages over previous techniques. For example, the present invention is capable of providing very high axial resolution (tens of nanometre). In addition, it is not necessary to measure the absolute intensity of the reflected light; the signal profile is instead used primarily to determine the apparent positions of the interfaces of the eye or other parts of the body. As such, the method is relatively less affected by atmospheric conditions and other changes to the outside of the eye. Furthermore, corneal changes, for example, may be de-convolved from the measurement of the apparent depth of the section. Also, a laser source is not essential for the present invention. Finally, scanning of the measurement region is not required enabling the measurement to be performed more quickly and the instrument to be more robust.

According to a second aspect of the present invention, there is provided an apparatus for measuring an apparent depth of a section of an animal body, the section being defined by first and second interfaces, comprising: a) an optical focusing assembly, comprising an optical element adapted to provide an expanded focal region for monochromatic light, the optical focusing assembly being adapted to focus an monochromatic incident beam of light to a plurality or continuum of measurement locations along a measurement line passing through the section, such that incident light is focused to all measurement locations along the measurement line concurrently; b) a detector assembly, adapted to detect light reflected from at least one of the plurality of measurement locations when a respective interface is coincident therewith and to generate a signal representative of that detected light; and c) a processor in communication with the detector assembly and adapted to receive from the detector assembly first and second signals corresponding to detected light reflected from the first and second interfaces respectively and to derive therefrom apparent positions of the first and second interfaces.

In preferred embodiments, the apparatus employs a confocal arrangement, so that the location from which the light is reflected may be precisely determined. In one embodiment the measurement location is scanned by translating a spatial filter on a scanning stage. In a preferred embodiment the extended focal region is obtained by focussing light with an axicon element.

According to a third aspect of the present invention, there is provided a method of measuring a property of an eye or other part of the body, comprising the steps of: a) generating an extended focal region within or proximate to the measurement region of interest; b) receiving reflected light from the measurement region; c) spatially filtering the reflected light in order to define a point location with the measurement region; d) scanning the measurement point with that region; e) measuring the intensity of reflected light received from each measurement point; f) relating an intensity measurement to an apparent position of the measurement location; g) selecting intensity measurements of interest representing measurement locations of interest; and h) determining a distance between the measurement locations of interest.

Preferably the measurement employs a spatial filter in the detector section that is confocal with the measurement point under investigation. Preferably the intensity measurements of interest are peaks in the reflected light intensity profile that is obtained, each peak representing a respective interface between different refractive regions of the eye or part of the body under investigation.

According to a fourth aspect of the present invention, there is provided an apparatus for measuring a property of an eye or other part of the body, comprising: a light source, a source optical element, adapted to direct light from the light source to the measurement location, an optical element adapted to give an extended focal region at the measurement location; a return optical element adapted to receive reflected light from the measurement location and to focus the reflected light to a receiver assembly, an optical detector, adapted to measure an intensity of the light received from each measurement position; and a processor, adapted to relate an intensity measurement to an apparent position of the measurement location, such that an apparent distance between measurement locations of interest, represented by respected intensity measurements of interest, may be derived.

Preferably, the apparatus employs a confocal scanning arrangement. Advantageously, a reference location is provided by a pinhole aperture, which also acts to stop stray light (i.e. light not reflected from the measurement position) from impinging on the detector.

The apparatus of the present invention may be used in a variety of applications. Preferably, the apparatus is compact and portable. In particular, the apparatus of the present invention may be formed of components using micro-electromechanical systems (MEMS), or micro-systems technology (MST), and may additionally or alternatively be incorporated in a hand-held device, and these features represent further aspects of the present invention.

Other preferred features are set out in the description, and in the dependent claims which are appended hereto.

BRIEF DESCRIPTION OF THE DRAWINGS

The present invention may be put into practice in a number of ways and some embodiments will now be described, by way of example only, with reference to the following figures, in which.

DETAILED DESCRIPTION OF THE DRAWINGS

Figure 1:
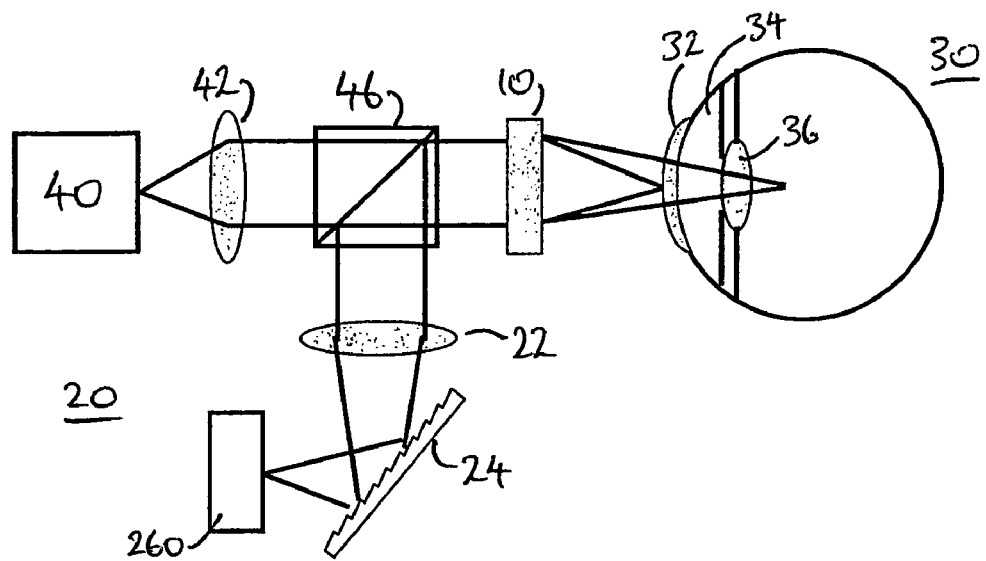
FIG. 1 shows schematically an optical arrangement for producing an extended focal region, in accordance with a first example.

FIG. 1 shows an example, not forming part of the claimed invention, but described for its use in understanding the invention and to enable the application of its principles to the invention. In FIG. 1, an expanded, or extended, focal region R is used to measure the apparent locations of interfaces within an eye 30. Incident light is focused to an axially extended region R by use of a suitable light-spreading element 10, which focuses the light to a plurality, or a continuum, of measurement locations V simultaneously. In FIG. 1, the extended region R is generally proximate with or within the eye 30. The axial focal region R extends through at least part of the eye 30 such as the anterior chamber of the eye. Along the extended focal region R, each time the focused light encounters an interface of the eye 30, light is reflected from the interface. The reflected light is then detected to generate a signal representative of that detected light and the apparent location from which the light is reflected is logged. The apparent location of the measurement volume or location V, as determined externally of the eye 30, is related to the signal, so that a reflected light signal profile, with respect to the apparent position of the measurement location, may be generated and, from this, the apparent locations of the interfaces determined. An optical path length, or depth, between any two interfaces of interest may then be calculated.

As the light from the light-spreading element 10 passes through an interface bounding two media of different refractive index n, the incident light is reflected from the surface. The interface is any surface from which light is reflected. In particular, the interface is a surface of a transparent medium having a different refractive index from its surroundings, such that a Fresnel reflection occurs when light is incident upon the surface. A light intensity detector assembly 20 detects the reflected light and generates a signal, which rises to a peak and then falls away each time an interface of the eye 30 is encountered. The size of the intensity spike depends on the properties of the two media either side of the interface. A reflection peak is therefore obtained, for example, for each of the four, main surfaces of the anterior chamber of the eye 30: the air-cornea boundary, the cornea-aqueous humor boundary, the aqueous humor-ocular lens boundary, and the ocular lens-vitreous humor boundary. The apparent distance between features of interest on the intensity curve may then be determined and properties of the eye 30, such as corneal thickness, ocular lens thickness, or optical path length, l, through the aqueous humor 34, may be derived.

The optical path length, l, through the aqueous humor 34 is given by the distance between the intensity peaks seen when the reflected light is from the cornea-aqueous humor interface and the aqueous humor-ocular lens interface. The intensity curve (of which an exemplary one is shown schematically in FIG. 3) is characteristic for the reflected light intensity measured between the exterior surface of the cornea 32 and the surface between the ocular lens 36 and the vitreous humor. As such, the two intensity measurements of interest are the middle two of the four, main peaks generated and the distance between these peaks will be referred to as the optical path length l.

The optical path length l is the product of the physical thickness, d, of the aqueous humor 34 and the refractive index, n, of the aqueous humor: l=nd. From individual to individual, the physical thickness d varies in dependence upon a number of factors, including the individual's particular physiology, the corneal thickness and the accommodation of the ocular lens 36. As a general rule, the cornea 32 increases in thickness by approximately 5% overnight and requires around four hours to return to its baseline thickness. A number of proposed techniques for the measurement of glucose levels in the aqueous humor 34 are affected by this phenomenon, to the extent that their accuracy is compromised. One advantage of the extended focal region technique of the present invention is that the corneal thickness may be measured independently and thus deconvolved from the measurement of the optical path length l of the aqueous humor 34.

Other factors which may affect the properties of the cornea 32, the aqueous humor 34 and the ocular lens 36 may also be deconvolved from the optical path length l measurements. For example, the wearing of contact lenses changes the thickness of the cornea 32. Using the extended focal region technique of the present invention, both this effect and the fact that an additional optical component is present along the measurement line may be taken into account and factored out of the optical path length l measurement. Similarly, by arranging for the measurement line—provided by the extended focal region R—to extend partially into the vitreous humor, the locations of both surfaces of the ocular lens 36 may be determined. The thickness of the ocular lens 36 can then be evaluated and taken into account in the optical path length l measurement. Alternatively, a reference object 38 (not shown) may be used to achieve a reference accommodation of the eye 30. By arranging the reference object 38 so that it appears to be located at infinity and so that it is visible by the eye 30 throughout a measurement, it is possible for the eye to maintain a constant, reference accommodation (i.e., the ocular lens 36 should repeatably adjust to substantially the same thickness when focusing the reference object 38). This also provides the advantage that the eye 30 is looking in a predetermined direction and not to one side (i.e., the eye is properly aligned), which helps to ensure that reflected light is properly received by the detector assembly 20.

If the physical thickness d of the aqueous humor 34 is constant, or if changes to its thickness caused by variations in the cornea 32 and/or the ocular lens 36 are measured and taken into account, any changes in the optical path length l measurement are due to changes in the refractive index n of the aqueous humor. Therefore, once a calibration measurement of the optical path length l, refractive index n, and physical thickness d of the aqueous humor has been taken, changes in the refractive index may be determined. Since there is a linear relationship between the concentration of glucose within the aqueous humor 34 and its refractive index n, changes in the glucose concentration may be derived from the changes in refractive index. Then, because the glucose concentration in the aqueous humor 34 is, in turn, dependent on the glucose concentration in the bloodstream of a patient, changes in the blood glucose concentration may be determined. In this way, the patient may check his blood glucose level and discover whether any corrective action is required, should the level be outside acceptable limits.

There are a number of ways of performing the patient calibration. One preferred method involves taking several measurements of the optical path length l and, for each measurement, also taking a blood sample, from which the blood glucose concentration may be derived. The range of measurements should cover the expected range of blood glucose concentrations of a diabetic patient. The optical path length l may be measured directly, but the physical thickness d and the refractive index n may not be resolved independently from a single optical path length measurement. It is therefore assumed that the physical thickness d does not change by an appreciable amount between measurements, so that there is a direct correlation between the range of measurements of the optical path length l and the derived blood glucose levels. The correlation curve, which is generally a straight line, may then be used for future optical path length measurements—taken without a corresponding blood sample—to determine the blood glucose concentration of the patient.

In FIG. 1, the extended, or expanded, focal region R is obtained by use of an element 10 that spreads the wavelengths from a broadband light source 40 axially along the focal region. In this embodiment light from the broadband source 40 is collimated and passes first through a beamsplitter 46 then through a diffractive, wavelength-spreading element 10 having a different focal length for each wavelength. One suitable element is a Fresnel zone plate. As a result there is an extended focal region R produced at the measurement region in the eye 30. If there is a surface at a particular point in the measurement region, it will reflect light back into the measurement instrument. This reflected light will be re-collimated by the wavelength-spreading element 10 and directed to a detector assembly 20 by the cube beamsplitter 46.

In this embodiment, the detector assembly 20 comprises a lens 22, which focuses the reflected light towards a linear detector array 260, a diffraction grating 24, which redirects the beam and spreads the constituent wavelengths laterally; and the linear detector array 260. The linear detector array 260 therefore receives a different wavelength at each point along its length. By studying the intensity on each pixel of the array, a measure is gained of the intensity of light that is returned at each wavelength. As each wavelength originates from a different axial location in the extended focal region R within the eye 30, it is possible to gain a measure of the intensity of the reflected light from each location in the eye and thereby to determine where interfaces of interest lie.

The advantage of this wavelength-based extended focal length technique is that it is not necessary to scan through the measurement region and so measurements may be made more quickly.

The wavelength-spreading element 10 may comprise either a Fresnel zone plate with a binary or grey scale intensity profile, or an element providing a surface relief diffractive effect. Again the surface relief profile may be either binary or continuously varying.

The beamsplitter 46 may be provided by a BK7 broadband AR coated 50/50 beam splitter, such as a 25 mm side Linos cube, number 35 5525 (manufactured by LINOS Photonics GmbH & Co. KG of Germany). However, in certain applications, a custom-made beam splitter may be used.

The term "beam splitter" is generally used to refer to an optical element which divides an incident light beam. The ratio of reflected light to transmitted light in any chosen direction may be adjusted according to the particular functional requirements of the beam splitter. In the present embodiment, the beam splitter 46 is arranged to permit 50% of the incident light beam to pass through the beam splitter, from the source collimating lens element 42 to the wavelength-spreading element 10, substantially undeviated. For light returning through the wavelength-spreading element 10, the beam splitter 46 is arranged to redirect 50% of the return light by 90° towards the detector assembly 20. In an alternative embodiment, a polarising beam splitter, followed by a quarter-wave plate is used, in order to reduce the amount of light lost during combination and redirection.

When a component feature of the eye 30, such as the air-cornea interface or the aqueous humor-ocular lens interface, lies along the measurement line, within the extended focal region R, an intensity peak is seen. For measuring the distance between features of interest of the eye 30, it is not necessary to measure the absolute intensity of the reflected light reaching the detector assembly 20; the information required is provided by the lateral position of the centre of each peak representing a feature of interest.

In order to improve the accuracy of the intensity measurements taken, curve fitting may optionally be used to increase the resolution with which the peak of each intensity spike is determined.

The distance between the intensity peaks generated by reflections from the back surface of the cornea 32 (the cornea-aqueous humor interface) and the front surface of the ocular lens 36 (the aqueous humor-ocular lens interface) represents the optical path length l through the aqueous humor 34. If the accommodation of the eye 30 is maintained throughout a measurement and is consistent for all measurements, then the physical depth of the aqueous humor is a constant and the only variable is the refractive index n of the aqueous humor. As such, changes in the refractive index n—measured as changes in the optical path length l—may be linked to changes in the glucose level. In order to achieve this, it is necessary first to perform an individual calibration for each patient, to ascertain the particular relationship between the optical path length l and the blood glucose concentration.

Figure 2:
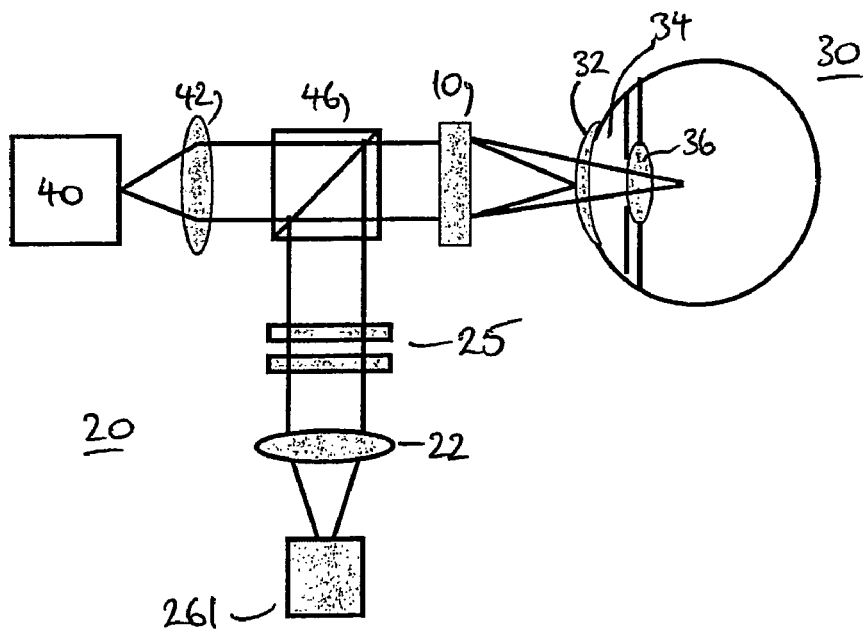
FIG. 2 shows schematically an optical arrangement for producing an extended focal region, in accordance with a second example.

FIG. 2 shows another example, not forming part of the claimed invention, but described for its use in understanding the invention and to enable the application of its principles to the invention. In FIG. 2, the detector assembly 20 comprises a Fabry-Perot etalon 25 and point detector 261, instead of a grating 24 and linear detector array 260. By scanning the distance between the etalon plates, the transmitted wavelength can be selected and its intensity detected by the receiver 261. The transmitted wavelength is related to the axial position of a reflecting surface and so the location of this surface can be determined.

Figure 3:
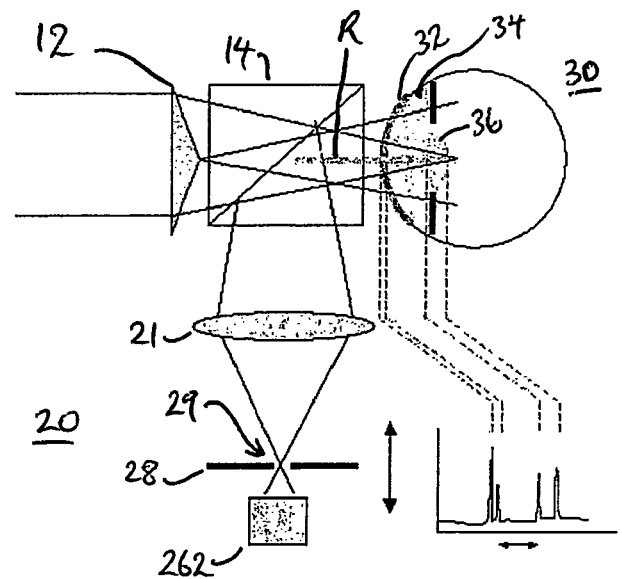
FIG. 3 shows schematically an optical arrangement for producing an extended focal region, in accordance with an embodiment of the invention.

FIG. 3 shows an embodiment of the present invention in which an extended focal region R is used to measure the apparent locations of interfaces within the eye 30. Incident light is focused to an axially extended region R generally proximate with or within the eye 30 by use of an optical element 12. In FIG. 3, the optical element 12 is an axicon. The axial focal region R extends through at least part of the eye and each time the focused light encounters an interface of the eye, light is reflected from the interface. The reflected light is then detected to generate a signal representative of that detected light.

The location from which the detected light is reflected, the measurement volume V, is determined by the use of a convergent lens 21 used in conjunction with a pinhole aperture 29 that only allows light to pass if it originated from a particular plane within the region under investigation. That is, the apparatus is arranged such that the measurement volume V is confocal with the pinhole aperture 29. The pinhole aperture 29 is provided by a pinhole stop 28, which is scanned so that reflected light can be detected from the whole of the measurement region R. The apparent location of the measurement volume V, as determined externally of the eye 30, is related to the signal, so that a reflected light signal profile, with respect to the apparent position of the measurement location, may be generated and, from this, the apparent locations of the interfaces determined. An optical path length, or depth, l, between any two interfaces of interest may then be calculated.

FIG. 3 shows a scanning pinhole stop 28 the location of which is confocal with the measurement location V. The scanning pinhole stop 28 may be scanned along its optical axis (not shown), so that the measurement location V from which reflected light is detected is, in turn, 'scanned' from a location external of the eye 30 to a location within the eye. With reference to the anterior chamber of the eye 30, the eye comprises a cornea 32, aqueous humor 34 and an ocular lens 36, behind which is the vitreous humor. In this embodiment, the line of measurement taken by the measurement location passes through the cornea 32, the aqueous humor 34 and the ocular lens 36. Throughout a measurement, light is focused by the axicon 12 to the entire extended focal region R (shown as a shaded line in FIG. 3) at all times. It is, therefore, the location of the pinhole aperture 29 which determines the location within the extended focal region R from which reflected light is actually detected. By translating the pinhole aperture 29 along a line, the entire extended focal region R may be analysed, if desired.

Preferably, in this embodiment, a light source 40 (not shown) provides an incident beam of light, which is collimated by an optical arrangement and passed through the axicon 12. The axicon 12 generates an intense, non-diverging region of light, having a peak intensity, which extends for a predetermined distance before dissipating rapidly. The axicon 12 comprises either a conical lens or rotationally symmetric prism and the term is used in this specification to encompass all such lens structures. Generally, axicons are used either to convert a collimated light beam into a ring; to create a non-diffractive Bessel beam; or to focus a collimated light beam over a long focal depth. It is the last feature of an axicon which is used to advantage in the present embodiment.

The incident light beam simultaneously illuminates the whole of the region of interest (i.e. the extended focal region R) and is reflected at surface boundaries where there is a refractive index difference. The reflected light is first redirected by a beam splitter 14 and then focused by a lens 21, towards the pinhole aperture 29. The extended focal region R will contain series of points, each of which is coincident respectively with a surface within the eye 30. The pinhole aperture 29 is scanned, such that the measurement volume V is effectively scanned through the extended focal region R. When the measurement volume V is coincident with an interface in the eye 30 and confocal with the pinhole aperture 29, a signal peak is detected by the detector assembly 20. The location within the eye 30 that is confocal with the pinhole aperture 29 is the measurement location V at any point in time during the scan.

The measurement location V is scanned along a measurement line through the eye 30, from a position in front of the cornea 32 to behind the ocular lens 36. During this operation, the apparent distance moved by the pinhole aperture 29 and the intensity values of the backward scattered light beam received at the detector assembly 20 are logged. Since light passing through the pinhole aperture 29 is received from the measurement location V, any light received at the detector assembly 20 should have been reflected from the measurement location and should, therefore, indicate the presence of an interface. Of course, there will be a relatively low, background level of light detected by the detector assembly 20, but the surface reflections will result in a much greater intensity signal, so there is no degradation in measurement accuracy as a result of this. The distance moved between the intensity peaks seen when the back surface of the cornea 32 and the front surface of the ocular lens 36 respectively are in focus gives the optical path length l through the aqueous humor 34.

Figure 4:
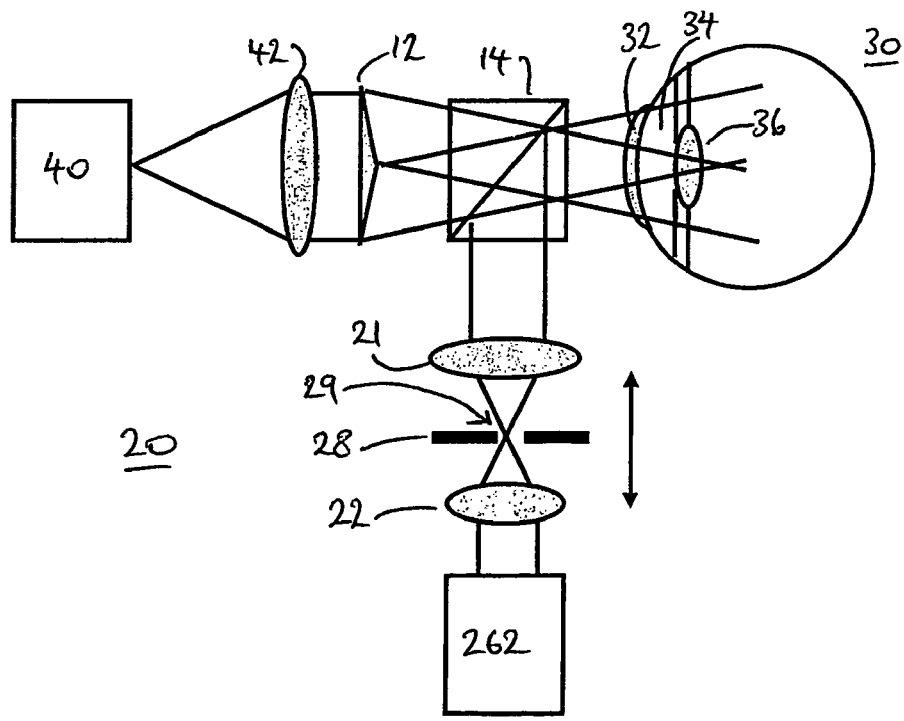
FIG. 4 shows schematically an optical arrangement employing the principles of that of FIG. 3.

FIG. 4 shows a further embodiment employing an axicon 12. Throughout this specification, identical or similar items are referred to using the same reference numeral. The apparatus comprises a monochromatic, light-emitting diode (LED) light source 40, which is arranged to emit light in the red region of the visible wavelength spectrum. Diodes which may be used include the Hamamatsu L7140 10 650 nm optical link LED (manufactured by Hamamatsu Photonics K. K. of Japan) or the Opto Diode Corporation OD 520 L high output green LED (manufactured by Opto Diode Corp. of California, USA), although, for certain applications, proprietary light sources may be designed and used. This wavelength region is chosen in order to minimise the possibility of causing chronic damage to the eye 30. In addition, red light is preferred, since there is a relatively large choice of LEDs in this wavelength region. However, light at other visible wavelengths, down to and including green light, may alternatively or additionally be used, especially for embodiments using two wavelengths of light (such as FIG. 5, below), since this offers a desirable separation between the two wavelengths.

A source collimating lens element 42 is located downstream of the light source 40 and is used to collimate the light into an incident light beam having a defined beam size. An axicon 12 is then used to generate the extended focal region R that illuminates the eye 30.

The measurement location V lies on a measurement line, which is coaxial with the optical axis of the axicon 12. Preferably, the optical axis of the eye 30 is also coaxial with the optical axis of the axicon 12, such that the measurement line passes from outside the eye, through the centre of the cornea 32, through the aqueous humor 34 and through the centre of the ocular lens 36. If desired, the measurement line may continue through the ocular lens 36 and partially into the vitreous humor, so that measurements of the thickness of the ocular lens may be taken.

If a surface of, or in, the eye 30 is present in the extended focal region R, provided by the axicon 12, incident light is reflected. The reflected light is focused by a pinhole convergent lens 21 to a scanning region of the pinhole stop 28. The point to which reflected light is focused will vary according to the location in the extended focal region R from which the light is reflected. When the pinhole aperture 29 is coincident with any particular point, the aperture is confocal with its respective location in the extended focal region R. If there is a reflecting surface at this location, there is a peak in the intensity of light received at the pinhole aperture 29. The detector assembly 20 measures the intensity of the return light, which is linked to the apparent measurement location by any suitable means, such as a processor 60.

The diameter of the pinhole aperture 29 is determined by the required numerical aperture (NA) of the incident light beam and the wavelength of light used. In this embodiment the diameter is of the order of 10 μm.

The pinhole stop 28 is mounted on a scanning stage 62 (not shown), so that it may be translated backwards and forwards. In this way, the measurement location V may be effectively scanned along the measurement line, through the eye 30 (although, in fact, there is no such scanning within the eye itself; it is merely the location from which reflected light is detected externally of the eye which is varied).

In order to obtain a reflected light intensity profile of the eye 30, the pinhole stop 28 is scanned by the scanning stage 62, so that the extended focal region R is analysed, from a point external of the eye, in front of the cornea 32, to a point within the ocular lens 36. While the scanning stage 62 translates the pinhole element 28, the position of the scanning stage is measured by a sensor 64 (not shown). This positional information is sent to a processor 60 (not shown), which also receives intensity signals from the detector assembly 20 and associates the two readings, so that the measurement volume V within the extended focal region R in relation to component features of the eye 30 is known throughout the measurement process.

Figure 5:
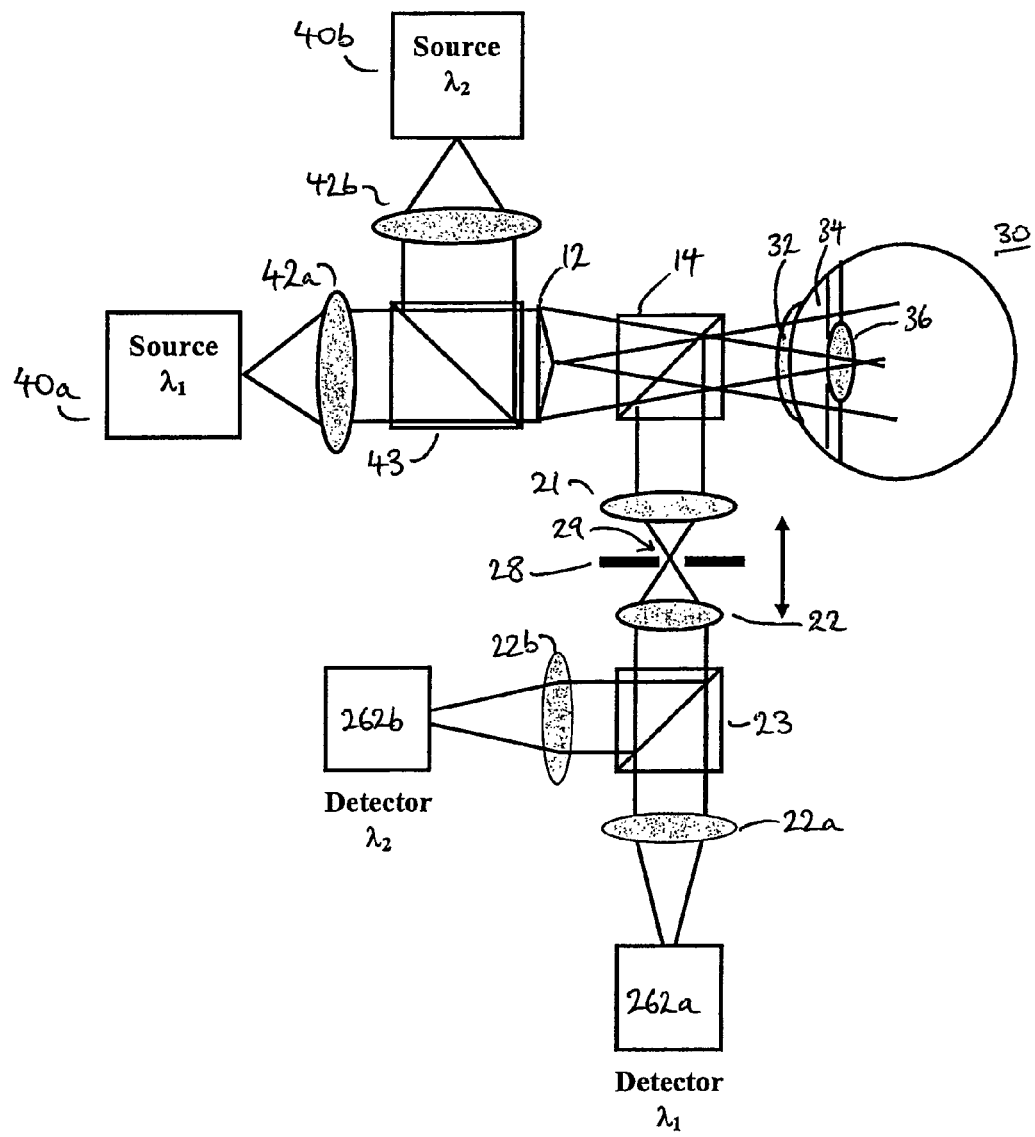
FIG. 5 shows schematically an optical arrangement employing the principles of the arrangements of FIGS. 3 and 4, but using two different wavelengths of light.

In order to provide increased resolution to the measurements and to make the ocular property-measuring instrument more useful, two wavelengths, $\lambda_1$ and $\lambda_2$, may be used to perform two optical path length measurements simultaneously. One such embodiment is shown in FIG. 5. The apparatus is similar to that shown in FIG. 4, but differs in the following details:

The light source 40 and source collimating lens element 42 have been replaced by a first light source 40a and first source collimating lens element 42a, a second light source 40b and second source collimating lens element 42b, and a beam combiner 43. These components are disposed upstream of the axicon 12, as before. The first and second light sources 40a, b and collimating lens elements 42a, b respectively are arranged such that their optical axes are mutually perpendicular. In this way, a first light beam having a first wavelength, $\lambda_1$, is received at the beam combiner 43 and a second light beam, having a second different wavelength, $\lambda_2$, is received at the beam combiner along an optical axis generally perpendicular to that of the first. The two light beams are combined and the combined light beam passes onwards in the manner described above. On reflection from a surface of the eye 30 and receipt by the beam splitter 14, the combined return light beam is redirected by substantially 90°, again as before. However, in this embodiment, a first detector convergent lens element 22a and detector 262a, a second detector convergent lens element 22b and detector 262b, and a detector beam splitter 23 are disposed downstream of the pinhole collimating lens element 22. Return light from the pinhole aperture 29 is received by the detector beam splitter 23, which separates the return light into two (still combined) perpendicular light beams, for focusing and detection. The first and second detectors 262a, b may comprise any suitable filter means (not shown) for permitting light of one wavelength only ($\lambda_1$ and $\lambda_2$ respectively) to be detected. Alternatively, the detector beam splitter 23 may separate the return light beam by wavelength and produce two light beams having the first and second wavelengths $\lambda_1, \lambda_2$ respectively.

As for the single wavelength measurement, the intensity profiles measured are matched to the measurement location V and the apparent location of the surfaces of interest in the eye 30 are determined for each wavelength. These independent measurements of the optical path length $l_1, l_2$ of the aqueous humor 34 are thus made, and from these measurements, two simultaneous equations may be obtained and solved. Since the refractive index n of the aqueous humor 34 varies with the wavelength of the incident light, the two simultaneous equations both include three variables: the refractive index $n_{\lambda,1}, n_{\lambda,2}$ at each wavelength $\lambda_1, \lambda_2$ and the thickness d of the aqueous humor 34. However, as the refractive indices $n_{\lambda,1}, n_{\lambda,2}$ are dependent on wavelength and are therefore related to each another, the two simultaneous equations may be solved and the refractive index and thickness of the aqueous humor 34 determined.

One approach for analysing the two equations obtained when two wavelengths, $\lambda_1, \lambda_2$, are used is as follows. The two equations obtained are:

$$l_1 = dn_{\lambda 1}$$

$$l_2 = dn_{\lambda 2}$$

where d is the (constant) physical thickness of the aqueous humor 34 and $l_1$ is the optical path length and $n_{\lambda 1}$ is the refractive index for wavelength $\lambda_1$, and $l_2$ is the optical path length and $n_{\lambda 2}$ is the refractive index for wavelength $\lambda_2$. Since the physical thickness d is the same in both cases and $l_1$ and $l_2$ are both measured, the two variables which are to be solved are $n_{\lambda 1}$ and $n_{\lambda 2}$. The two refractive indices $n_{\lambda 1}, n_{\lambda 2}$ are related to each other by the dispersion curve for the particular concentration of glucose solution in the aqueous humor 34, the relationship taking the form:

$$D = f(n_{\lambda 1}/n_{\lambda 2}).$$

Therefore, by using a look-up table, or equation for the dispersion relation for different glucose concentrations, the ratio of the refractive indices $n_{\lambda,1}, n_{\lambda,2}$ at the two wavelengths $\lambda_1, \lambda_2$ can be used to calculate the glucose concentration of the aqueous humor 34.

Removing the physical distance d from this calculation provides an important benefit, since this value cannot accurately be assumed to be constant in all circumstances. In practice, the cornea 32 changes thickness diurnally, the ocular lens 36 oscillates regularly by a small amount and, during testing, a user may unintentionally move the test instrument or his head. Because both wavelength measurements are taken simultaneously, any variation in the value of the physical thickness d of the aqueous humor 34 will affect both measurements of the optical path length l equally and will therefore be cancelled out upon division of the two measurements.

As will be understood, the optical path length measurements need to be calibrated for each patient before use. This is achieved by simultaneously taking finger stick blood tests and performing the eye measurement, while the blood glucose level is varied. In this way, the blood glucose level may be directly related to the measured optical path length, or refractive index ratio, without the need to determine the intermediate values of the glucose concentration of the aqueous humor itself.

In addition, by using more than two wavelengths of incident light, it is possible to determine still other properties of the eye 30, such as the levels of ascorbate, pyruvate, lactate, and other chemicals, including medically or intentionally introduced drugs as well as naturally occurring ones. It is also possible to determine refractive index changes taking place as a result of changes in ambient temperature and pressure. In this way, N simultaneous equations may be generated, with N independent variables, and these may be solved to determine changes in properties of the eye 30. If m different properties of the aqueous humor 34, for example, are to be evaluated, m+1 substantially discrete measurement wavelengths should be used.

Principles behind the extended focal region technique embodied by the apparatus of FIG. 4 and the apparatus of FIG. 5 will now be described in some detail with reference to FIGS. 6a and 6b.

Figure 6A:
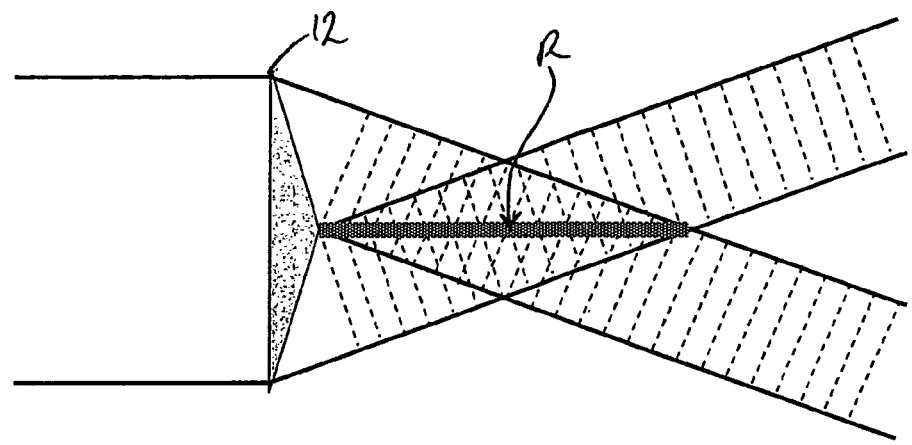
FIGS. 6a and 6b illustrate highly schematically the technique of producing an extended focal region.

FIG. 6a illustrates the standard technique of using an axicon, a conical lens or rotationally symmetric prism, to generate a focal region with an extended, high-intensity core R. The axicon 12 is illuminated with a collimated light beam and refracts the light such that it converges towards the optical axis (not shown), but with a constant numerical aperture across the beam-front. The result, seen in cross section, is two plane beams that interfere to generate a high-intensity core along the optical axis. This is shown in FIG. 6a as the dark shaded region R.

Figure 6B:
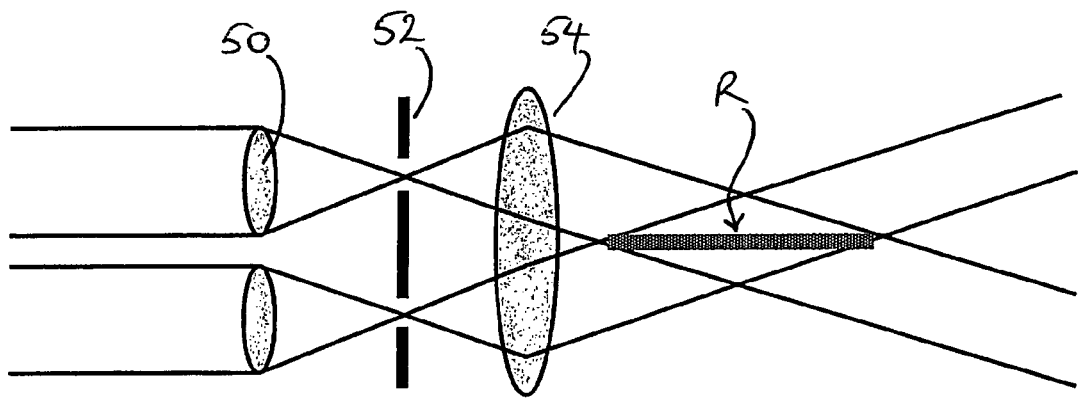

In an alternative embodiment, shown in FIG. 6b, an annular lens 50, annular mask 52 and collimating lens 54 assembly is used. With the conical lens arrangement, the intensity in the extended focal region R increases with distance from the axicon 12 up to the point where the region ends. By using an annular lens, annular mask, and collimating lens assembly, the on-axis intensity profile is constant. The annular lens 50 focuses the light into and through the transparent region of the annular mask 52. The collimating lens 54 then redirects the light into the same pattern as would a conical lens. In practice, as both arrangements comprise an aperture formed by a lens, the Fresnel diffraction effects cause the intensity profile along the axis to be chirped, that is to oscillate slightly in intensity. As the oscillation is by a known amount this effect does not alter the measurement procedure.

A particular advantage of the use of a Bessel beam, such as that generated by an axicon, for the measurement process is that the central peak is continually regenerated. As the continual overlapping of the generating light reconstitutes the central peak, any faults or debris in the eye 50, such as floaters, do not affect the focal region further into the eye.

Depending on the presence of, and exact location of, a reflecting object within the extended focal region R at a measurement volume V confocal with the pinhole aperture 29, the intensity measured by the detector assembly 20 will be either a negligibly small, minimum value (for no object), a peak value (for an object coincident with the measurement region), or a value between the minimum and peak values (for an object close to the measurement region). As the measurement region, within the extended focal region R, from which reflected light is detected is effectively moved towards the reflecting object, the intensity value rises, in line with the object coming increasingly into focus. Thus, by scanning the pinhole aperture 29, an intensity curve may be generated. Therefore, by knowing the location of the pinhole stop 28 during translation, the exact position of the measurement region V may also be known.

Thus by knowing the design of the optical arrangement and the relative position of the pinhole aperture 29, the apparent location of the reflecting object may be established by determining the distance measurement which corresponds with the peak intensity measurement on the curve. The use of the confocal principle in this configuration permits a reference location in space to be defined very precisely. Indeed, it is possible to achieve sub-micrometre axial resolution using such a confocal arrangement.

Figure 7:
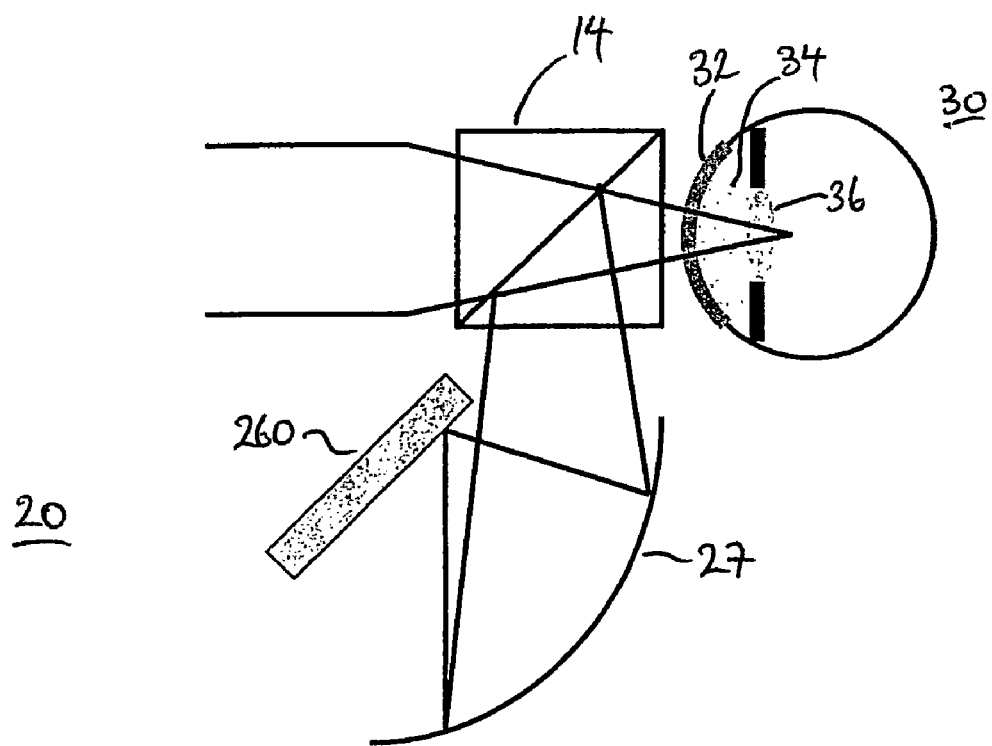
FIG. 7 shows schematically an optical arrangement employing a concave mirror and linear detector array, in accordance with a further embodiment.

In a further embodiment, the detector assembly 20 is altered so that no scanning is required. In this embodiment, shown in FIG. 7, the light returning through the beam splitter 14 is focused onto a linear detector array 260, using an off-axis focusing mirror 27. The light returning from each part of the extended focal region R is linearly separated by the focusing mirror 27, so that different locations in the measurement region are detected by different locations of the linear detector array 260. By analysing the detector array 260, the intensity of light returning from each axial location of the extended focal region R is determined and the location of the interfaces ascertained, according to the intensity profile thereby obtained.

The extended focal region technique, various embodiments of which have been described above, may also be used to detect debris in the aqueous humor 34, caused for example by corrective eye surgery, cataract removal and the like. Currently, such debris is not specifically quantified and ophthalmologists have different views as to what is to be considered a large or small amount of material. With the above technique, the debris is detected as small intensity reflections within the aqueous humor 34 and the number and size of these reflections may be used to quantify the amount of such debris in the aqueous humor.

In order to obtain a strong return signal at the detector assembly 20, it is important that the eye 30 is oriented to be axially aligned with measurement apparatus. In one embodiment, this is achieved by simultaneously projecting an image 38 to the user whilst taking the measurement, so that the user focuses on this image and the correct alignment and accommodation of the eye 30 is maintained. In an alternative embodiment, two points of light, coaxial with the measurement beam, are projected into the eye 30, so that the user may align the two points before performing the measurement, thereby ensuring correct alignment. In yet another embodiment, a point source of light, coaxial with the measurement beam, is directed to the eye 30. Only when the user lines up the light (i.e. when the user can see the point source of light) is the instrument correctly aligned.

Axial misalignment results in the return light beam being slightly offset with respect to the optical element 10, 12 and thus reduces the level of return light received by the detector assembly 20. If, however, a CCD array is used, each pixel within the CCD array can be treated as a pinhole aperture. Accordingly, if the focused return light moves to one side, the pixel considered to be the pinhole aperture may be replaced by a different pixel, thereby tracking the focused return light by tracking the intensity peak. There will be a generally larger background level of light in this case, but the intensity peak may still be detected and tracked by analysing the detected intensities measured by the neighbouring pixels in the array.

Figure 8:
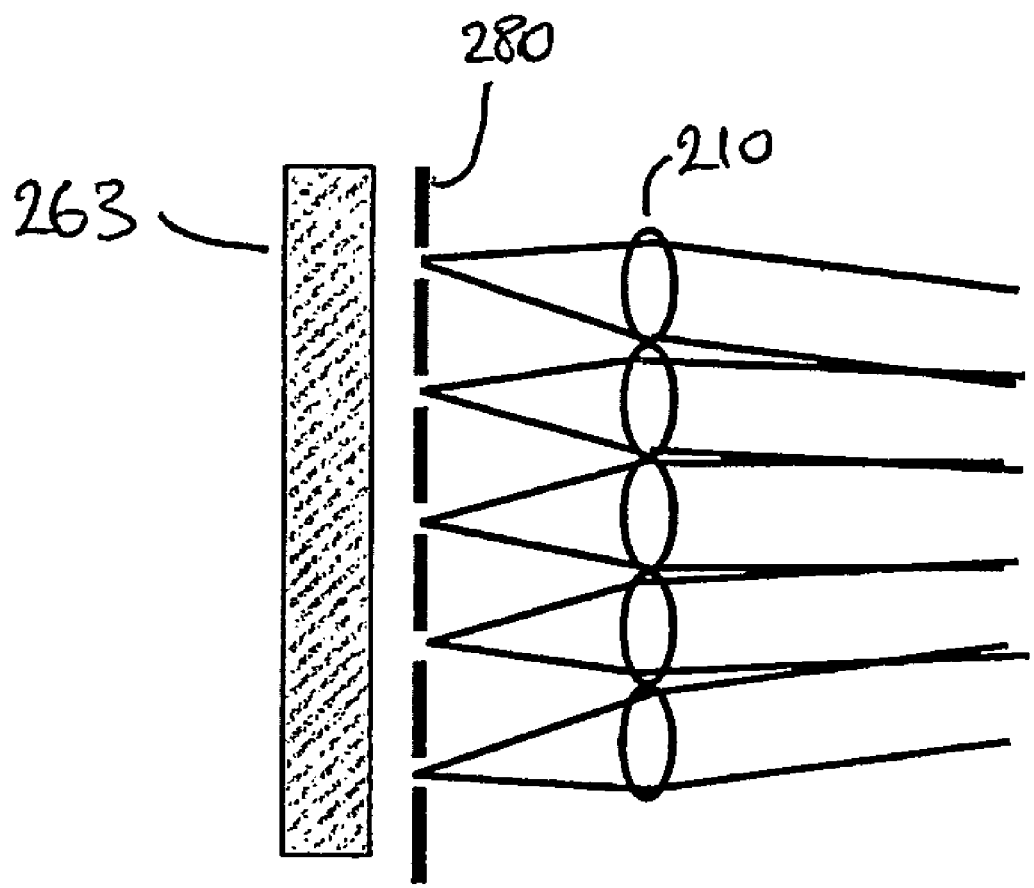
FIG. 8 shows schematically a micro-lens array, a pinhole array, and detector array assembly, in accordance with a still further embodiment.

Alternatively, a further solution to the axial misalignment problem which does not require the user to look straight into the instrument involves the use of an array of micro-lenses 210, in combination with an array of pinhole apertures 280 in the return path and a CCD detector array 263, as shown in FIG. 8. With this arrangement, an array of confocal detectors is provided, with each individual confocal system being arranged to analyse a specific angle of the return light.

It will be understood that the above embodiments can be adapted and enhanced in a number of ways. From a patient's point of view, it may be disconcerting to have a laser shone into an eye, so it is preferable for the apparatus to use an incoherent light source 40. This is acceptable from a functionality perspective, but alternative embodiments may use laser sources. These can be any form of laser, including but not limited to diode lasers, vertical cavity surface emitting lasers (VCSELs) and gas lasers. The narrow waveband of a laser source has the advantage that any chromatic aberrations occurring in the optical system with an incoherent source 40 may be reduced, if desired.

In embodiments using an incoherent light source 40 the source may be either a narrow or broad wavelength band type. The possible sources include but are not limited to light emitting diodes (LEDs), incandescent or fluorescent lights, or any broadband, "white light" source. With a broadband source, a wavelength filter, such as an etalon, diffraction grating, thin film filter, de-multiplexer (as used in optical telecommunications), or other design could be used to define a narrow measurement waveband, if desired. This filter may be located at or near the source 40 or the detector assembly 20 of the instrument.

There is no specific restriction to the wavelength of light which may be used to perform the measurements, although, in particular for monochromatic measurements, wavelengths in the red region of the spectrum are preferable, since these minimise the possibility of any long term effects on the eye. The wavelength may alternatively be in the ultraviolet, visible, near infra-red or far infra-red region of the spectrum, in any desired range.

The optical elements used in the instrument are preferably refractive lenses, but in some instances it may be advantageous to use diffractive elements instead. Diffractive elements generally have a shallower profile than the refractive elements and may be easily mass produced by moulding techniques, which offers advantages when large scale production is intended. Alternatively still, graded index lenses may be used, and these have the advantage that they are of high quality, relatively small and economical to use in high quantities.

Although in some of the above embodiments the measurement location V is confocal with a pinhole aperture 29, the pinhole aperture may alternatively be provided by one or more fibre optic or other light guide elements. The use of an optical fibre affords the possibility of providing the apparatus in the form of a test instrument body and remote test head. As such, the test instrument body could, for example, be located on the earpiece of a pair of spectacles, with the test head being built into the front of the spectacles. The use of a light guide structure permits greater flexibility in terms of the location and direction of the light beams than with free-space optics.

The detector 260-263 employed in the instrument may be one of a number of detectors using silicon or other technology, such as a CCD, CMOS, or APD, although others are not excluded. The desirable criteria for the detector 260-263 are that the detector has a large dynamic range, to be able to distinguish the intensity peaks from the background, and that the response time is fast enough to capture the intensity reading from each point in space as the measurement location V is "scanned" through it. The detector assembly 20 may comprise a single element, a linear array, or a two-dimensional array. If a two-dimensional array is used, each pixel may be interrogated independently and axial misalignment of the eye 30 can be accounted for. In such an embodiment, the system may be configured without a physical pinhole stop 28, since each pixel within a CCD detector, for example, can be treated as the equivalent of a pinhole aperture 29.

While it is preferable for the incident light beam to be reflected so that the return light beam passes back at least partially along the original path taken by the incident light beam—that is, part of the return lens arrangement through which the return light beam passes is preferably provided by part of the objective lens arrangement through which the incident light beam passes, since this reduces the size and complexity of the instrument—the reflected light beam may be arranged to be focused along a different path. This may be achieved, for example, by disposing the objective lens arrangement to one side of the optical axis of the eye 30 and disposing the return lens arrangement equally and oppositely on the other side of the optical axis of the eye.

In any case, the lens arrangements preferably comprise a compound lens.

Depending on the particular requirement of the ocular property-measuring apparatus, the light source 40 may be arranged to generate light having one of a static, jittered, swept or stepped wavelength. This may be achieved in various ways, including the use of a variable wavelength laser, a diffraction grating, a spectrometer, an etalon, or a wavelength division multiplexer.

The measurement technique may be enhanced by using interferometry, in which a second incident light path is used in the measurement apparatus and the two beams are interfered coherently, thereby producing an interference pattern which may be measured. The polarisation of the incident light beam may also be controlled, so that more than one polarisation state is used to perform the measurement and two or more simultaneous equations are obtained. In this way, again, more than one parameter of the eye 30 may be measured. Another possible means for obtaining two or more simultaneous equations so that more than one property of the eye 30 may be measured is to provide an array of optical systems in parallel.

This may be achieved with a micro-lens array 210, in conjunction with a pinhole array 280, arranged to provide an array of confocal test systems, as illustrated in FIG. 8. Light received through the array of pinhole apertures 280 is detected by a detector array 263, such as a CCD detector array.

In order to improve the axial resolution of the measurements taken by the instrument, the incident light beam may be modulated and the detector 20 provided with phase sensitive detection means.

Alternatively, other techniques may be used to define a position in space. Optical coherence tomography (OCT) uses a low coherence source and Michelson interferometer arrangement, in which the reference lens is scanned through the required spatial distance to produce an interference effect and a high intensity response, when the optical path length in the reference arm matches that in the working arm and a reflection is obtained from a surface of the eye 30.

The apparatus of the present invention is intended for use in a number of settings, such as in a hospital or a laboratory, by a doctor or an optician, or privately by an individual patient.

As such, the apparatus of the present invention may be fitted onto an optical bench or an examination table (as used by an optician for example), or the apparatus may be more mobile, for use by a patient, either while at home or outside. In particular, the apparatus of the present invention may be contained within a hand-held device and may additionally be battery powered. One particularly advantageous embodiment of the present invention involves the use of micro-electromechanical systems (MEMS), or micro-systems technology (MST). The use of micro-optics, micro-motors and micro-stages to achieve a small apparatus size offers particular benefits when the apparatus of the present invention is used as a hand-held device.

Alternative applications of the extended focal region measurement technique of the present invention include the use of infra-red light to illuminate and pass through the skin of a human or other animal and thereby investigate the structure, thickness and depth of items below the skin's surface. These could include but are not limited to cancers, cysts, blood clots and other both naturally occurring and purposely introduced items.

As will be understood, there are many different embodiments which may be used to put the apparatus and method of the present invention into practice. Those described above are by way of example only and many alternatives are envisaged and intended to form part of the present invention.

The invention claimed is:

1. A method of measuring an apparent depth of a section of an animal body, the section being defined by first and second interfaces, comprising the steps:
   a) focusing a monochromatic incident beam of light to a plurality or continuum of measurement locations along a measurement line passing through the section, the measurement line being generated by an optical element adapted to provide an extended focal region for monochromatic light, such that incident light is focused to all measurement locations along the measurement line concurrently;
   b) detecting light reflected from at least one of the plurality of measurement locations when a respective interface is coincident therewith;
   c) generating at least a first and a second signal representative of the detected light reflected from the first and second interfaces respectively; and
   d) deriving from the first and second signals the apparent positions of the first and second interfaces.

2. The method of claim 1, wherein the section is the aqueous humor of an eye and the apparent depth is an optical path length through the aqueous humor.

3. The method of claim 2, wherein the first interface is a surface between the cornea and the aqueous humor of the eye and the second interface is a surface between the aqueous humor and the ocular lens of the eye.

4. The method of claim 2, further comprising the step of comparing the derived apparent depth with a previous reference measurement of the apparent depth, and determining a change in the refractive index of the aqueous humor.

5. The method of claim 4, further comprising the step of calculating a measure of change in a concentration of glucose within the bloodstream of a patient from the change of refractive index.

6. The method of claim 1, wherein the detected light comprises substantially only light which has been focused to a measurement location and reflected by an interface coincident therewith.

7. The method of claim 1, wherein the optical element is an axicon lens.

8. The method of claim 1, wherein the reflected light is detected after being received at a pinhole aperture adapted to be translatable through a range of positions confocal with respective ones of the plurality of measurement locations, such that light reflected from ones of the measurement locations having a respective interface coincident therewith may be detected by scanning the pinhole aperture through the range.

9. The method of claim 1, further comprising the step of generating light having two or more wavelengths, for measuring two or more properties of the section of an animal body.

10. An apparatus for measuring an apparent depth of a section of an animal body, the section being defined by first and second interfaces, comprising:
    a) an optical focusing assembly, comprising an optical element adapted to provide an expanded focal region for monochromatic light, the optical focusing assembly being adapted to focus a monochromatic incident beam of light to a plurality or continuum of measurement locations along a measurement line passing through the section, such that incident light is focused to all measurement locations along the measurement line concurrently;
    b) a detector assembly, adapted to detect light reflected from at least one of the plurality of measurement locations when a respective interface is coincident therewith and to generate a signal representative of that detected light; and
    c) a processor in communication with the detector assembly and adapted to receive from the detector assembly first and second signals corresponding to detected light reflected from the first and second interfaces respectively and to derive therefrom apparent positions of the first and second interfaces.

11. The apparatus of claim 10, wherein the processor is further adapted to compare the derived apparent depth with a previous reference measurement of the apparent depth, such that a change in the refractive index of the section may be determined.

12. The apparatus of claim 10, wherein the optical element is an axicon lens.

13. The apparatus of claim 10, wherein the detector assembly comprises a pinhole aperture and a detector, the pinhole aperture being adapted to be translatable through a range of positions confocal with respective ones of the plurality of measurement locations, such that light reflected from one of the measurement locations having a respective interface coincident therewith may be detected by scanning the pinhole aperture through the range.

14. The apparatus of claim 10, further comprising a light source, adapted to produce the incident beam of light and being further adapted such that the light has one of a substantially single wavelength or a plurality of substantially discrete wavelengths.

* * * * *